US00RE38628E1

(19) United States
(12) Reissued Patent
Clark et al.

(10) Patent Number: US RE38,628 E
(45) Date of Reissued Patent: Oct. 19, 2004

(54) PHARMACEUTICAL COMPOSITIONS

(75) Inventors: Andrew R. Clark, Half Moon Bay, CA (US); Paul Wright, Bramcote (GB); Julia H. Ratcliffe, Woodbridge (GB)

(73) Assignee: Fisons plc, Ipswich (GB)

(21) Appl. No.: 08/916,578

(22) Filed: Aug. 22, 1997

Related U.S. Patent Documents

Reissue of:
(64) Patent No.: 5,443,833
Issued: Aug. 22, 1995
Appl. No.: 08/082,804
Filed: Jun. 25, 1993

U.S. Applications:
(

(63) Continuation of application No. 07/742,574, filed on Aug. 7, 1991, now abandoned, which is a continuation of application No. 07/410,020, filed on Sep. 20, 1989, now abandoned, which is a continuation of application No. 07/133,520, filed on Dec. 16, 1987, now abandoned.

(30) Foreign Application Priority Data

| | | |
|---|---|---|
| Dec. 23, 1986 | (GB) | 8630767 |
| Dec. 23, 1986 | (GB) | 8630769 |
| Dec. 24, 1986 | (GB) | 8630904 |
| Mar. 20, 1987 | (GB) | 8706684 |

(51) Int. Cl.[7] ..... A61F 13/00
(52) U.S. Cl. ..... 424/434; 424/400; 424/489; 424/451; 424/427
(58) Field of Search ..... 424/434, 489, 424/451, 427, 43, 400; 514/311, 912

(56) References Cited

U.S. PATENT DOCUMENTS

| | | | | |
|---|---|---|---|---|
| 4,328,341 | A | * | 5/1982 | Raphael et al. |
| 4,419,352 | A | * | 12/1983 | Cox et al. |
| 4,474,787 | A | * | 10/1984 | Cairns et al. |
| 4,698,345 | A | * | 10/1987 | Dicker et al. |
| 4,760,072 | A | * | 7/1988 | Brown et al. |
| 4,849,427 | A | * | 7/1989 | Nassim et al. |
| 4,866,072 | A | * | 9/1989 | Edwards et al. |
| 4,868,192 | A | * | 9/1989 | Totten et al. |

FOREIGN PATENT DOCUMENTS

| | | | |
|---|---|---|---|
| GB | 2022078 | * | 12/1979 |
| GB | 2157291 A | * | 4/1985 |
| JP | 0004722 | * | 1/1983 |

OTHER PUBLICATIONS

Patel, K.R. "Dose–Response Study of Sodium Cromoglycate in Exercise–Induced Asthma", Thorax, vol. 37, pp. 663–666.*

Br. J. Clin. Pharmac. vol. 24, Oct. 1987, pp. 493–501, M.G. Neale, et al "The Pharmacokinetics of Nedocromil Sodium, a New Drug for the kinetics of Nedocromil Sodium, a New Drug for the Treatment of Reversible Obstructive Airways Disease, in Human Volunteers and Patients with Reversible Obstructive Airways Disease".*

J. Med. Chem. vol. 28, No. 12, 1985, pp. 1832–1842, American Chemical Society, H. Cairns, et al., New Anti-allergic Pyrano (3,2–g) quinoline 2,8dicarboxylic Acids with Potential for the Topical Treatment of Asthma.*

J. Allergy Clin. Immunol. vol. 79, No. 1, Feb. 19–25, 1987, p. 186, abstract 247, Schwartz et al. "Efficacy of nedocromil sodium . . . ragweed seasonal allergic rhinitis (SAR)".*

J. Allergy Clin. Immuno. vol. 80, No. 2, Aug., 1987, pp. 218–222, Corrado et al., "The effect of nedocromil sodium on nasal provocation with allergen."*

J. Allergy Clin. Imunol., vol. 81, No. 3, Mar. 1988, pp. 570–574 Ruhno et al. "Intranasal nedocromil sodium in the treatment of ragweed–allergic rhinitis."*

Invest. Ophtalmol. Visual Sci. vol. 29, May 1–6, 1988, p. 229, Stockwell et al, "Double blind group comparative trial of 2% nedocromil . . . seasonal allergic conjunctivitis."*

Pharmazie, vol. 37, No. 4, 1982, pp. 261–263 Pohloudek–Fabini et al, "Zur Stabilitat der Phenylquecksilbersalze."*

Journal of Pharmaceutical Sciences, vol. 65, No. 4, Apr. 1976, pp. 628–630, Grady, et al, "Testing of heat sealing by thermal analysis."*

R. Voight, "Lehrbuch der pharmazeutischen Technologie", 5th edition, 1984, pp. 554–557, Verlag Chemie, Weinheim, D.E.*

P.H. List: "Arzneiformenlehre" Chapter Konservierungmittel pp. 369–373, 1976.*

P.H. List: "Arzneiformenlehre" Chapter Augenarzneien pp. 400–410, 1976.*

R. Voight: "Lehrbuch der pharmazeutischen Technologie" Chapter 27 Augentropfen, pp. 459–467, 1975.*

Eur. J. Respir. Dis. (Suppl. 147) 1986, pp. 120–131, R.M. Auty: "The Clinical development of a new agent for the treatment of airway inflammation, nedocromil sodium (Tilade)."*

* cited by examiner

*Primary Examiner*—Thurman K. Page
*Assistant Examiner*—Robert M. Joynes
(74) *Attorney, Agent, or Firm*—Jon Hokanson, Esq.; Coudert Brothers LLP

(57) ABSTRACT

A method of treatment of a condition selected from the group comprising conjunctivitis, keratitis, 'allergic eyes', adenovirus infections, corneal homograft rejection, anterior uveitis, nasal polyps, vasomotor rhinitis, allergic manifestations of the nasopharynx, reversible obstructive airways disease, Crohn's disease, distal colitis and proctitis, which method comprises administration to a patient suffering from such a condition of a therapeutically effective amount of an aqueous solution containing, as active ingredient, 9-ethyl-6,9-dihydro-4,6-dioxo-10-propyl-4H-pyrano(3,2-g) quinoline-2,8-dicarboxylic acid or a pharmaceutically acceptable salt thereof. Also described are novel pharmaceutical compositions suitable for use in such methods of treatment.

13 Claims, No Drawings

PHARMACEUTICAL COMPOSITIONS

Matter enclosed in heavy brackets [ ] appears in the original patent but forms no part of this reissue specification; matter printed in italics indicates the additions made by reissue.

This is a Continuation of U.S. application Ser. No. 07/742,574, filed Aug. 7, 1991, now abandoned; in turn a Continuation of Ser. No. 07/410,020 filed Sep. 20, 1989, now abandoned; in turn a Continuation of Ser. No. 07/133,520 filed Dec. 16, 1987, now abandoned.

FIELD OF THE INVENTION

This invention relates to methods of treatment and to novel pharmaceutical compositions for use in such methods.

DESCRIPTION OF THE PRIOR ARTS

In British Patent No 2022078 there are disclosed a number of pyranoquinoline compounds which are indicated for use in the treatment of reversible airway obstruction. Pharmaceutical compositions containing these compounds are also described, especially compositions in which the active ingredient is in powder form with a mass median diameter of from 0.1 to 10 microns. British Patent Application No 2157291A describes the particular utility of the disodium salt of one of these compounds, 9-ethyl-6,9-dihydro-4,6-dioxo-10-propyl-4H-pyrano(3,2-g)quinoline-2,8-dicarboxylic acid, in the treatment of reversible airway obstruction. Also described are powdered aerosol compositions of this salt for administration to the lung and physical forms of the salt which are especially suitable for formulation in this way.

BRIEF SUMMARY OF THE INVENTION

We have now surprisingly found that when it is administered in aqueous solution the same compound is efficacious in the treatment of a variety of disorders of the eye, notably conjunctivitis, as well as in the treatment of certain disorders associated with other organs.

Thus, according to the invention there is provided a method of treatment of a condition selected from the group comprising:

- conjunctivitis, keratitis, 'allergic eyes', adenovirus infections, corneal homograft rejection, anterior uveitis;
- nasal polyps, vasomotor rhinitis, allergic manifestations of the nasopharynx;
- reversible obstructive airways disease;
- Crohn's disease, distal colitis and proctitis, which method comprises administration to a patient suffering from such a condition of a therapeutically effective amount of an aqueous solution of 9-ethyl-6,9-dihydro-4,6-dioxo-10-propyl-4H-pyrano(3,2-g)quinoline-2,8-dicarboxylic acid or a pharmaceutically acceptable salt thereof.

By the term 'conjunctivitis' we mean inflammatory disorders of the conjunctiva commonly characterised by photophobia and irritation. The condition may be bacterial or vital and encompasses a number of specific types of conjunctivitis; for instance, seasonal allergic conjunctivitis, perennial allergic conjunctivitis, vernal catarrh (vernal kerato-conjunctivitis) , 'irritable eye' or 'non-specific conjunctivitis', Herpes Simplex Conjunctivitis, Herpes Zoster Conjunctivitis and phlyctenular conjunctivitis.

Similarly, by the term 'keratitis' we mean inflammation of the cornea which may involve its superficial surface ('superficial keratitis' including the localised form known as 'corneal ulceration') or be confined to the deeper layers ('interstitial keratitis'). Other particular forms of keratitis which may be mentioned include Herpes Simplex Keratitis and Herpes Zoster Keratitis.

Proctitis includes chronic (ie ulcerative) and non-specific proctitis.

DETAILED DESCRIPTION OF THE INVENTION

Pharmaceutically acceptable salts of the active ingredient include salts with metal cations, such as alkali metal cations. We particularly prefer the disodium salt which is commonly referred to as nedocromil sodium.

The solution is administered by a route appropriate to the condition being treated. For instance, administration may be to the eye, intra-nasally (e.g. as a nasal spray), by inhalation as a nebulised cloud or rectally as an enema.

We prefer administration of the solution to be by a route other than by inhalation. In particular, we prefer administration to be to the eye.

The solution may contain from about 0.1 to 10% w/v of the active ingredient. However, we prefer the active ingredient to be present at a level of less than 5% and more particularly less than 3% w/v, e.g. 0.5%, 1.0% or 2.0% w/v. The concentration of choice will depend of course inter alia on the nature of the conditions to be treated, its severity and the mode of administration of the solution.

In addition to the active ingredient the solution generally contains one or more pharmaceutically acceptable additives. Examples of classes of additive which may be present are:

a) chelating or sequestering agents, b) preservatives, and c) viscosity-modifying agents.

Suitable chelating or sequestering agents include sodium carboxymethyl cellulose, citric, tartaric or phosphoric acid, and amino carboxylate compounds. The preferred chelating agent, however, is ethylenediamine tetraacetic acid or a salt thereof, especially its di-sodium salt.

The concentration of the chelating or sequestering agent should be such as to ensure that no precipitate of metal salts of the active ingredient occurs. A suitable concentration of chelating or sequestering agent may be from 0.005 to 0.5, e.g. 0.01 or 0.1% w/v.

The choice of preservative, where the solution contains a preservative, may depend on the route of administration. Preservatives suitable for solutions to be administered by one route may possess detrimental properties which preclude their administration by another route. For nasal and ophthalmic solutions, preferred preservatives include quaternary ammonium compounds, in particular the mixture of alkyl benzyl dimethyl ammonium compounds known generically as 'Benzalkonium Chloride'. For solutions to be administered by inhalation, however, the preferred preservative is chlorbutol. Other preservatives which may be used, especially for solutions to be administered rectally, include alkyl esters of p-hydroxybenzoic acid and mixtures thereof, such as the mixture of the methyl, ethyl, propyl and butyl esters which is sold under the tradename "Nipastat".

The concentration of preservative should be such as to ensure effective preservation of the solution ie such that bacterial growth in the solution is inhibited. For most preservatives the concentration will typically lie in the range 0.001 to 0.1% w/v. However, in the case of chlorbutol acceptable concentrations are greater than 0.25% but less than 0.6% w/w ie the concentration of chlorbutol is 0.25 to 0.6%, preferably 0.3 to 0.55% e.g. 0.5% w/w.

Suitable viscosity enhancing agents which may be incorporated into the solution include carbomers ie polymers of acrylic acid cross-linked with a polyalkenyl polyether, aluminum magnesium silicate, methylcellulose, hydroxypropyl methylcellulose and other cellulose derivatives.

The viscosity of the solution will depend, inter alia, on the particular viscosity enhancing agent used and its molecular weight and on the target organ. However, the solution preferably has a viscosity of at least 100 cps, more preferably at least 200 cps and especially more than 400 cps, at a shear rate of 50 $s^{-1}$. The viscosity of the solution is preferably less than 10000 cps, more preferably less than 1000 cps and especially less than 500 cps, at a shear rate of 50 $s^{-1}$.

Viscosities are preferably determined using a rotational viscometer such as a Rheomat 30 (Rheomat is a Trade Mark), at a temperature of from 15° to 25° C. e.g. 20° C.

For applications which involve the solution being administered as a spray e.g. through a nasal pump, we prefer the viscosity enhancing agent to have a low viscosity at high shear rates, e.g. from about 100 cps to about 300 cps at 140 $s^{-1}$, and a high viscosity at low shear rates, e.g. from about 700 cps to about 1200 cps at 15 $s^{-1}$.

Viscosity enhancing agents which we prefer include hydroxypropyl methylcellulose and carbomers, in particular the carbomer sold as Carbopol 934, the viscosity of a neutralised 0.5% w/w aqueous dispersion of which lies in the range 29400 to 39400 cps and the heavy metal content of which is 0.002% or less.

The amount of viscosity-modifying agent required to achieve the desired viscosity will depend on the particular agent used and also on its molecular weight. However, we prefer to use up to about 2% w/w, e.g. 0.5 to 1.5% w/w of viscosity enhancing agent.

The solution may also contain other conventional excipients, e.g. sodium chloride, dextrose or mannitol, and buffers, e.g. sodium dihydrogen orthophosphate (sodium acid phosphate BP), di-sodium hydrogen phosphate (sodium phosphate BP) sodium citrate/citric acid, and boric acid/sodium borate. The proportion and concentration of excipients and buffers may be varied within fairly wide ranges, provided the resulting solution is stable and non-irritant when applied to the appropriate tissues. The maximum total concentration of excipients and buffers is preferably less than 5% w/v and more preferably less than 2% w/v. Solutions for rectal administration may contain bulking agents, e.g. methyl cellulose, to aid retention in the bowel.

The solution may be made isotonic with physiological fluids by the incorporation of a suitable tonicity agent e.g. sodium chloride. The solution typically contains from about 0.1 to 1.0, more typically 0.5 to 1.0% w/v sodium chloride.

Although physiological pH is about 7.4, we prefer the pH of the solution to be in the range 3.5 to 6, preferably 4 to 5.5. In this range of pH, the stability of the solution is enhanced, surprisingly with no deleterious effects such as undue tissue irritation.

The composition of the invention may be made up, for example, by dissolving the active ingredient, chelating or sequestering agent (if included) and excipients (if included) in freshly distilled water, adding to this solution an aqueous solution containing the preservative (if included), adjusting the pH if necessary, making the solution up to the desired volume with distilled water, stirring and then sterilising. Alternatively, the active ingredient, chelating or sequestering agent (if included) and excipients (if included) may be dissolved in a solution containing the preservative. Sterilisation is preferably performed by sterile filtration into a previously sterilised container. Where the preservative used is benzalkonium chloride, some complex formation may occur when the solutions of active ingredient and preservative are mixed. It may thus be necessary to use a higher concentration of preservative than is desired for the final product.

Aqueous solutions containing active ingredient, a viscosity enhancing agent, e.g. a carbomer, and, optionally, a preservative, e.g. benzalkonium chloride, may be prepared by dispersing the viscosity enhancing agent in an aqueous solution containing the preservative (if used) and the active ingredient, and then, if required, adjusting the pH, e.g. by addition of sodium hydroxide, and, if desired, further diluting the solution with water.

The solution of the preservative and the active ingredient may be made simply by dissolving the ingredients in water which is low in metal ions.

The solution is preferably made up at a temperature of from about 10° to 50° C., for example at room temperature.

The solution may be put up in unit dosage form, in which case preservatives may be incorporated, but are generally not necessary. Alternatively the solution may be put up in multi-dose form. In general it will be necessary to incorporate one or more preservatives into multi-dose solutions to ensure that the solution remains sterile after initial use.

Conventionally, unit doses of aqueous solutions for use in nebulisers are packed in glass or plastics ampoules which are broken open immediately prior to use. Such packaging is both wasteful and expensive to manufacture. Furthermore, the breaking-open of glass ampoules could lead to the formation of glass sherds which can be inhaled with the solution.

We have now found a form of packaging for single-dose solutions which overcomes the above-mentioned disadvantages. Thus, according to a further aspect of the invention, we provide a soft ampoule of plastics material sterile-filled with a unit dose of an aqueous solution containing, as active ingredient, 9-ethyl-6,9-dihydro-4,6-dioxo-10-propyl-4H-pyrano(3,2-g)quinoline-2,8-dicarboxylic acid or a pharmaceutically acceptable salt thereof, and sealed.

We prefer the plastics material to be permeable to carbon dioxide. Thus, when the ampoule is stored, carbon dioxide dissolves in the solution and the pH is lowered. Since the stability of the active ingredient is greater at lower pH, this has the effect of enhancing the stability of the solution.

Suitable plastics materials from which the ampoule may be manufactured include low-density polyethylene.

A plurality of ampoules may be connected to, and formed integrally with, an anchorage member which may be adapted to receive a label or writing, e.g. to identify the contents of the ampoules.

The plastics material may include a pigment or pigments such that the ampoules correspond in colour to the solution contained within them.

Multi-dose solutions may be packaged in volumes of 5 to 300 ml. Preferred volumes for inhalation compositions include 60, 120 and 240 ml. For nasal and ophthalmic compositions multi-dose packs preferably contain from 5 to 20 ml of solution.

We prefer multi-dose solutions to be packaged such that unit volumes of the solution to be administered can be accurately dispensed. The solution may, for example, be packaged in a flexible-walled container provided with a cap to receive the unit volume.

The dosage to be administered will of course vary with the condition to be treated, with its severity and with its location. However, in general for use in the eye a dosage of about 1 or 2 drops (e.g. from about 0.3 to 1.2 mg of active ingredient depending on the concentration of active ingredient) into the affected eye from 2 to 4 times a day is found to be satisfactory. More frequent dosage may, of course, be used if desired. For use in the nose a dosage of about 0.25 ml (e.g. from about 1.2 mg to 5.0 mg of active ingredient) is indicated.

For rectal administration a total daily dosage of from about 50 to 1000 mg of active ingredient, more preferably 100 to 400 mg, administered in smaller doses 2 to 4 times a day is found to be satisfactory. A dosage unit may conveniently contain from about 25 to 200 mg of active ingredient.

For administration by inhalation a daily dosage of from about 10 mg to 100 mg is, in general, found to be satisfactory. The daily dosage may be administered in divided doses, e.g. from 2 to 4 times a day. More frequent dosage may of course be used if required.

The aqueous solutions according to the present invention are advantageous in that they are longer acting, more acceptable to the patient, give rise to higher concentrations of active ingredient in target tissues, give rise to effective concentrations of active ingredient in target tissues for a longer time or are more stable than known similar formulations.

The invention is illustrated, but in no way limited, by the following Examples.

Example 1

Non-preserved nebuliser solution

| | |
|---|---|
| Nedocromil Sodium | 0.5% w/v |
| Sodium Chloride | 0.79 |
| Hydrochloric acid | q.s. |
| Purified Water | to 100 |

Nedocromil sodium (5 g) and sodium chloride (7.9 g) were dissolved in purified water (900 ml). The pH of the solution was adjusted to between 5 and 5.5 by addition of hydrochloric acid and the volume made up to 1000 ml with purified water.

The solution was sterile-filled into low-density polyethylene ampoules which were then sealed.

Example 2

Preserved nebuliser solution

| | |
|---|---|
| Nedocromil Sodium | 0.5% w/v |
| Sodium Chloride | 0.79 |
| Chlorbutol | 0.5 |
| Sodium hydroxide | q.s. |
| Purified Water | to 100 |

Chlorbutol (5 g) was dissolved in purified water (900 ml). Nedocromil sodium (5 g) and sodium chloride (7.9 g) were then added to the solution. The pH of the solution was adjusted to between 5 and 5.5 by addition of sodium hydroxide and the volume made up to 1000 ml with purified water.

The solution was filled into polyethylene bottles of 120 ml capacity.

Example 3

Nasal Solution

| | |
|---|---|
| Nedocromil Sodium | 1.00% w/v |
| Sodium Chloride | 0.715 |
| Disodium Edeate | 0.01 |
| Benzalkonium Chloride | 0.02 |
| Purified Water | to 100 |

Nedocromil sodium (100 g), sodium chloride (71.5 g) and disodium edetate (1 g) were dissolved in approximately 5 liters of purified water. To this solution a dispersion of benzalkonium chloride solution 50% USNF (4 g) in approximately 1 liter of purified water was added. The solution was made up to 10 liters with purified water, stirred for 30 minutes, filtered to remove any complex formed and then sterile filtered and filled into bottles.

Example 4

Opthalmic Solution

| | |
|---|---|
| Nedocromil Sodium | 2.00% w/v |
| Benzalkonium Chloride | 0.01 |
| Disodium Edetate | 0.05 |
| Sodium Chloride | 0.55 |
| Purified Water | to 100 |

Prepared by the method of Example 3 above.

Example 5

Viscous Nasal or Opthalmic Solution

| | |
|---|---|
| Nedocromil sodium | 1.0% w/v |
| Disodium edetate | 0.1 |
| Benzalkonium chloride | 0.01 |
| Carbopol 934F | 0.73 |
| Sodium hydroxide | q.s. |
| Purified water | to 100 |

20 g of nedocromil sodium and 2 g of disodium edetate were dissolved in approximately 600 g of purified water. A dispersion of 0.808 g of Benzalkonium Chloride Solution 50% USNF in approximately 200 g of purified water was added and the resulting dispersion made up to 1000 g with purified water and stirred for 30 minutes.

The dispersion was filtered through a glass fibre pre-filter and the first 100 ml discarded. The remainder of the filtered solution was filtered through a pre-sterilised 0.22 um membrane filter and the filtrate collected.

250 g of the filtrate was added to 4.15 g of Carbopol 934P and stirred until the Carbopol was fully dispersed. The pH of the dispersion was adjusted to between pH 5.5 and 5.8 by addition of 2M sodium hydroxide solution. The dispersion was mixed until a homogeneous uniform gel was formed. The gel was made up to 500 g with purified water, remixed and filtered through a 13 um stainless steel filter.

The viscosity of the solution at 20° C. and a shear rate of $50s^{-1}$ was found to lie in the range 420–480 cps.

Example 6

Enema Solution

| | |
|---|---|
| Nedocromil Sodium | 0.15% w/v |
| Nipastai | 0.10 |
| (Nipastai is a trademark) | |
| Sodium Chloride | 0.812 |
| Purified Water | to 100 |

Methyl cellulose or other agents may be added to aid retention of the solution in the bowel.

Example 7

Study of 2% Nedocromil Sodium Eye-Drops in the Treatment of Seasonal Allergic Conjunctivitis 32 patients (11 male, 21 female) with ages in the range 4 to 69 (average 25.2) participated in an investigation of the efficacy of an aqueous solution of nedocromil sodium in the treatment of seasonal allergic conjunctivitis. The solution used had the composition given in Example 4. One drop (0.04 ml) was administered per eye four times a day for four weeks.

At the end of the trial, both the patient and the supervising clinician were asked to rate the effectiveness of the treatment, using the following 0–3 scale:

0=no control symptoms

1=slight control

2=moderate control

3=full control

In addition the patients were asked whether the eye-drops were an acceptable form of treatment.

For the 23 patients who completed the trial, the results were as follows:

| | No of patients | |
|---|---|---|
| Rating | Patients' assessment | Clinicians' assessment |
| 3 | 10 | 7 |
| 2 | 9 | 9 |
| 1 | 2 | 4 |
| 0 | 1 | 1 |

(One patient failed to record an opinion, and the clinician failed to record an opinion for two patients).

18 of the 23 patients recorded that they found the treatment acceptable.

We claim:

1. A method of treating a reversible obstructive airways disease comprising administering, by inhalation, to a patient suffering from, or susceptible to, such a condition the nebulized contents of an ampoule of carbon dioxide permeable plastics material filled with a unit dose of an aqueous pharmaceutical solution containing, as active ingredient, from 0.1 to 5% w/v of 9-ethyl-6,9-dihydro-4,6-dioxo-10-propyl-4H-pyrano(3,2-g)quinoline-2,8-dicarboxylic acid or a pharmaceutically acceptable salt thereof, the solution having a pH of 3.5 to 6.0.

2. The method of treatment according to claim 1, wherein the concentration of the active ingredient in the solution is from 0.1 to 1.0% w/v.

3. The method of treatment according to claim 1, wherein the active ingredient is nedocromil sodium.

*4. A method of controlling the symptoms of conjunctivitis comprising administering to the eye of a patient having conjunctivitis an effective amount of nedocromil sodium in an ophthalmically acceptable formulation.*

*5. The method of claim 4, wherein the conjunctivitis is vernal conjunctivitis.*

*6. The method of claim 4, wherein the conjunctivitis is allergic conjunctivitis.*

*7. The method of claim 4, wherein the conjunctivitis is seasonal allergic conjunctivitis.*

*8. A method of treatment of a disease selected from the group consisting of conjunctivitis, keratitis, allergic eyes, and anterior uveitis, which method comprises administering to the eye an effective amount of an ophthalmically acceptable aqueous pharmaceutical solution containing the active ingredient 9-ethyl-6,-dihydro-4,6-dioxo-10-propyl-4H-pyrano(3,2g)quinoline-2,8-dicarboxylic acid, or a pharmaceutically acceptable salt thereof.*

*9. The method of claim 8, wherein the disease is conjunctivitis.*

*10. The method of claim 9, wherein the disease is seasonal allergic conjunctivitis.*

*11. The method of claim 9, wherein the disease is allergic conjunctivitis.*

*12. The method of claim 9, wherein the disease is vernal conjunctivitis.*

*13. The method of claims 8, 9, 10, 11 or 12, wherein said active ingredient is nedocromil sodium.*

* * * * *